US005705364A

United States Patent [19]
Etcheverry et al.

[11] Patent Number: 5,705,364
[45] Date of Patent: Jan. 6, 1998

[54] MAMMALIAN CELL CULTURE PROCESS

[75] Inventors: Tina Etcheverry, Berkeley; Thomas Ryll, San Mateo, both of Calif.

[73] Assignee: Genentech, Inc., South San Francisco, Calif.

[21] Appl. No.: 469,348

[22] Filed: Jun. 6, 1995

[51] Int. Cl.⁶ .................................................. C12N 5/06
[52] U.S. Cl. ........................ 435/70.3; 435/383; 435/395; 435/375
[58] Field of Search ............................... 435/70.3, 240.2, 435/240.27, 240.3, 375, 383, 395

[56] References Cited

U.S. PATENT DOCUMENTS

| | | |
|---|---|---|
| 4,724,206 | 2/1988 | Rupp et al. . |
| 5,096,816 | 3/1992 | Maiorella . |
| 5,122,469 | 6/1992 | Mather et al. . |
| 5,151,359 | 9/1992 | Miyahara et al. . |
| 5,316,938 | 5/1994 | Keen et al. . |
| 5,447,851 | 9/1995 | Beutler et al. ............................ 435/69.7 |
| 5,510,261 | 4/1996 | Goochee et al. . |

FOREIGN PATENT DOCUMENTS

| | | |
|---|---|---|
| 0 239 292 A1 | 9/1987 | European Pat. Off. . |
| 0307247 | 3/1989 | European Pat. Off. . |
| 387840 | 9/1990 | European Pat. Off. . |
| 0481791A2 | 4/1992 | European Pat. Off. . |
| 1-257492 | 10/1989 | Japan . |
| 2122207 | 1/1984 | United Kingdom . |
| 2 153 830 | 8/1985 | United Kingdom . |
| 2251249 | 7/1992 | United Kingdom . |
| WO89/04867 | 6/1989 | WIPO . |
| WO94/06476 | 3/1994 | WIPO . |

OTHER PUBLICATIONS

Evans et al. (1994) J. Exp. Med. vol. 180(6) :2173–9.
Peppel et al. (1991) J. Exp. Med. vol. 174:1483–1489.
C. Waymouth, "Osmolality of mammalian blood and of media for culture of mammalian cells", *In Vitro*, 6(2), 109–127 (1970).
A. Corti et al, "Identification of differentially glycosylated forms of the soluble p75 tumor necrosis factor (TNF) receptor in human urine", *European Cytokine Network*, 6(1), 29–35 (1995).
A. Ashkenazi et al., "Protection against endotoxic shock by a tumor necrosis factor receptor immunoadhesin", *Proc. Natl. Acad. Sci. USA*, 88, 10535–10539 (1991).
Andersen et al., "The Effect of Ammonium Ion on the O–Linked Glycosylation of Granulocyte Colony–Stimulating Factor Produced by CHO Cells" *Abstracts of Papers, American Chemical Society* pp. 169 (1993).
Borys et al., "Ammonia Affects the Glycosylation Patterns of Recombinant Mouse Placental Lactogen–I By Chinese Hamster Ovary Cells in a pH–Dependent Manner" *Biotechnology and Bioengineering* 43:505–514 (1994).
Borys et al., "Culture pH Affects Expression Rates and Glycosylation of Recombinant Mouse Placental Lactogen Proteins by Chinese Hamster Ovary (CHO) Cells" *Bio/Technology* 11:720–724 (1993).

Chotigeat et al., "Role of Environmental Conditions on the Expression Levels, Glycoform Pattern and Levels of Sialytransferase for hFSH Produced by Recombinant CHO cells" *Cytotechnology* 15:217–221 (1994).
Cox et al., "Effect of Media Composition on the Induction of Chorionic Gonadotropin by Sodium Butyrate in HeLa Cells" *In Vitro* 19(1):1–6 (1983).
Curling et al., "Recombinant Human IFN–γ Produced by CHO Cells: Effects of Culture Environment on Product Quality" *Harnessing Biotechnology for the 21st Century* pp. 308–310 (1992).
D'Anna et al., "Concentration–Dependent Effects of Sodium Butyrate in Chinese Hamster Cells: Cell–Cycle Progression, Inner–Histone Acetylation, Histone H1 Dephosphorylation, and Induction of an H1–like Protein" *Biochemistry* 19:2656–2671 (1980).
Engelmann et al., "Effect of Sodium Butyrate on Primary Cultures of Adult Rat Hepatocytes" *In Vitro Cellular & Developmental Biology* 23(2):86–92 (1987).
Exley et al., "Monoclonal antibody to TNF in severe septic shock" *Lancet* 335:1275–1276 (1990).
Forman et al., "Control of Osmolality in Mammalian Cell Cultures: Reduction of Lactic Acid Accumulation Throughout On–line Control of Glucose Concentration" *Abstracts of Papers, American Chemical Society*, 207th ACS National Meeting p. 135 (1994).
Garcia–Perez et al., "Molecular Cloning of cDNA Coding for Kidney Aldose Reductase" *Journal of Biological Chemistry* 264(28):16815–16821 (1989).
Gawlitzek et al., "Changes in the Glycosylation Pattern of Recombinant Proteins Effected by Defined Culture Conditions of BHK–21 Cells" *Animal Cell Technology* pp. 649–651 (1989).
Goochee et al., "Bioprocess Factors Affecting Glycoprotein Oligosaccharide Structure" *DNA and Cell Biology* 76:95–104 (1992).
Goochee et al., "Environmental Effects on Protein Glycosylation" *Bio/Technology* 8:421–427 (1990).

(List continued on next page.)

*Primary Examiner*—David Saunders
*Assistant Examiner*—Emma Cech
*Attorney, Agent, or Firm*—Heller Ehrman White & McAuliffe

[57] ABSTRACT

The present invention relates to novel process for the preparation of glycoproteins by mammalian cell culture wherein the sialic acid content of the glycoprotein produced is controlled over a broad range of values by manipulating the cell culture environment. The invention provides for processes in which the sialic acid content of the glycoprotein is modified by changes in cell culture parameters which affect cell specific productivity. Preferred embodiments of the invention include cell culture processes in the osmolality of the cell culture is controlled as well as the concentration of a transcription enhancer during the production phase of the cell culture. The invention further provides for novel preparations of soluble type 1 tumor necrosis factor immunoglobulin G1 and their uses in the treatment of inflammatory or immune related disorders.

21 Claims, 2 Drawing Sheets

OTHER PUBLICATIONS

Goochee et al., "The Oligosaccarides of Glycoproteins: Bioproces Factors Affecting Oligosaccharide Structure and Their Effect on Glycoprotein Properties" *Bio/Technology* 9:1347–1355 (1991).

Goochee et al., "The Oligosaccharides of Glycoproteins: Factors Affecting Their Synthesis and Their Influence on Glycoprotein Properties" *Frontiers in Bioprocessing II* pp. 199–240 (1992).

Gorman et al., "Expression of Recombinant Plasmids in Mammalian Cells is Enhanced by Sodium Butyrate" *Nucleic Acids Research* 11(21):7631–7648 (1983).

Gramer et al., "Potential for degradation of glycoprotein oligosaccharides by extracellular glycosidases" *Am. Chem. Soc.* (Abstract, 203rd Meeting, San Francisco, CA) PT 1:BIOT–71 (Apr. 5, 1992).

Hagopian et al., "Effect of n–Butyrate on DNA Synthesis in Chick Fibroblasts and HeLa Cells" *Cell* 12:855–860 (1977).

Hart, "Glycosylation" *Current Opinion in Cell Biology* 4:1017–1023 (1992).

Hayter et al., "Glucose–Limited Chemostat Culture of Chinese Hamster Ovary Cells Producing Recombinant Human Interferon–γ" *Biotechnology and Bioengineering* 39:327–335.

Hearing et al., "Isolation of Chinese Hamster Ovary Cells Lines Temperature Conditional for the Cell–Surface Expression of Integral Membrane Glycoproteins" *The J. of Cell Biology* 108:339–353 (1989).

Howard et al., "Soluble Tumor Necrosis Factor Receptor: Inhibition of Human Immunodeficiency Virus Activation" *Proc. Natl. Acad. Sci. USA*, 90:2335–2339 (1993).

Huang et al., "On–line determination of glucose concentration throughout animal cell cultures based on chemiluminescent detection of hydrogen peroxide coupled with flow––injection analysis" *Journal of Biotechnology* 18:161–162 (1991).

Klehr et al., "Scaffold–Attached Regions (SAR Elements) Mediate Transcriptional Effects Due to Butyrate" *Biochemistry* 31:3222–3229 (1992).

Kobata et al., "Structures and Functions of the Sugar Chains of Glycoproteins" *European Jouranl of Biochemistry* 209:483–501 (1992).

Le Gros et al., "The Effects of Sodium Butyrate on Lymphokine Production" *Lymphokine Research* 4 (3) :221–227 (1985).

McClure et al., "Glucose Requirement for Induction by Sodium Butyrate of the Glycoprotein hormone α Subunit in HeLa Cells" *Archives of Biochemistry & Biophysics* 233(1) :93–105 (1984).

Milhaud et al., "Sodium Butyrate Affects Expression of Fibronectin on CHO Cells: Specific Increase in Antibody––Complement–Mediated Cytotoxicity" *J. Cellular Physiology* 104(2) :163–170 (1980).

Mizutani et al., "High Glucose and Hyperosmolarity Increase Platelet–derived Growth Factor mRNA Levels in Cultured Human Vascular Endothelial Cells" *Biochemical and Biophysical Research Communications* 187(2):664–669 (1992).

Ozturk et al., "Effect of Medium Osmolarity on Hybridoma Growth, Metabolism, and Antibody Production" *Biotechnology and Bioengineering* 37:989–993 (1991).

Parekh, "Effects of Glycosylation on Protein Function" *Current Opinion in Cell Biology* 1:750–754 (1991).

Park et al., "Enhanced β–Galactosidase Production by High Cell–Density Culture of Recombinant Bacillus subtilis with Glucose Concentration Control" *Biotechnology and Bioengineering* 40:686–696 (1992).

Paulson, "Glycoproteins: What are the Sugar Chains for?" *TIBS* pp. 272–276 (1989).

Peppel et al., "A tumor necrosis factor (TNF) receptor–IgG heavy chain chimeric protein as a Bivalent antagonist of TNF activity" *Journal of Experimental Medicine* 174:1483–1489 (1991).

Prasad et al., "Effect of Sodium Butyrate on Mammalian Cells in Culture: A Review" *In Vitro* 12(2) :125–132.

Sliwkowski et al., "Effect of Culture Conditions on Carbohydrate Charge Heterogeneity of Recombinant Human Deoxyribonuclease Produced in CHO Cells" *American Chemical Society Abstracts* BIOT 72:72 (1992).

Stubblefield et al., "Effects of Sodium Chloride Concentration on Growth, Biochemical Composition, and Metabolism of HeLa Cells" *Cancer Research* 20:1646–1655 (1960).

Tracey et al., "Anti–cachectin/TNF monoclonal antibodies prevent septic shock during letal bacteraemia" *Nature* 330:662–664 (1987).

Ulich et al., "Short Communication: Intratracheal Administration of Edotoxin and Cytokines IV. The Soluble Tumor Necrosis Factor Receptor Type I Inhibits Acute Inflammation" *American Journal of Pathology* 142 (5) :1335–1338 (1993).

Urlaub et al., "Isolation of Chinese Hamster Cell Mutants Deficient in Dihydrofolate Reductase Activity" *Proc. Natl. Acad. Sci. USA* 77(7) :4216–4220 (Jul. 1980).

Varki, "Biological Roles of Oligosaccharides: All of the Theories are Correct" *Glycobiology* 3:97–130 (1993).

Werner et al., "Mammalian Cell Cultures Part II: Genetic Engineering, Protein Glycosylation<Fermentation and Process Control" *Arzneim–Forsch./Drug Res.* 43(II) :1242–1249 (1993).

Wittwer et al., "Glycosylation at Asn–184 Inhibits the Conversion of Single–Chain to Two–Chain Tissue–Type Plasminogen Activator by Plasmin" *Biochemistry* 29:4175–4180 (1990).

Wooley et al., "Influence of Recombinant Human Soluble Tumor Necrosis Factor Receptor FC Fusion Protein on Type II Collagen–Induced Arthritis In Mice" *The Journal of Immunology* pp. 6602–6607 (1993).

Yuan et al., "Effect of Butyrate on the Expression of Microinjected or Transfected Genes" *J. Biol. Chemistry* 260(6) :3778–3783 (1985).

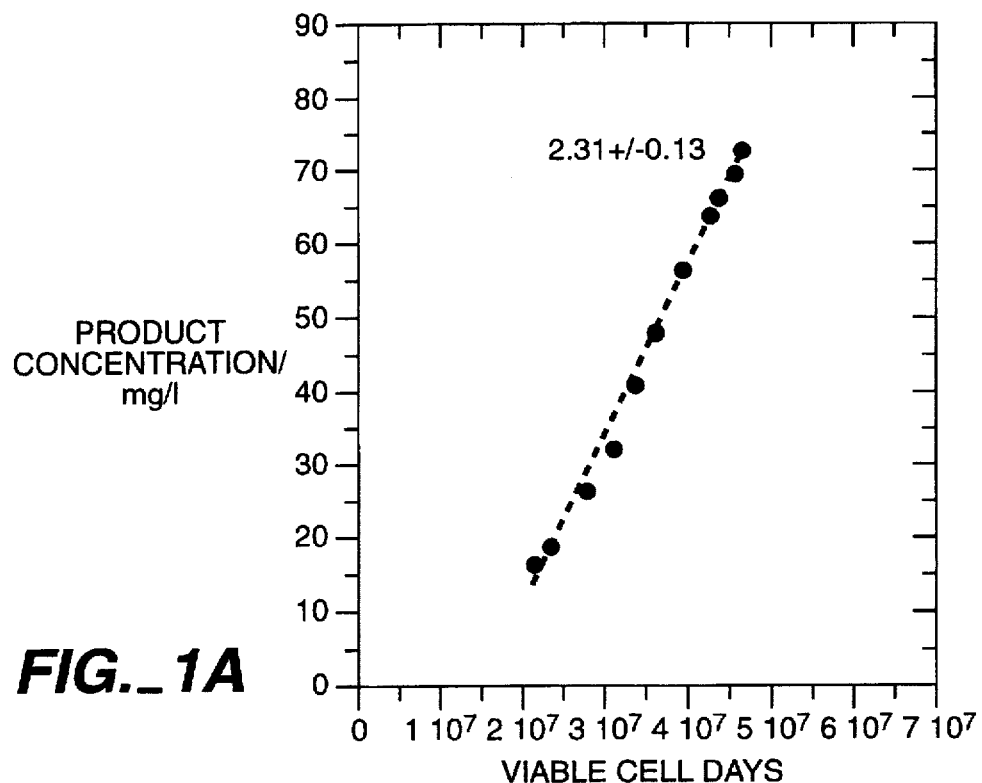
FIG._1A
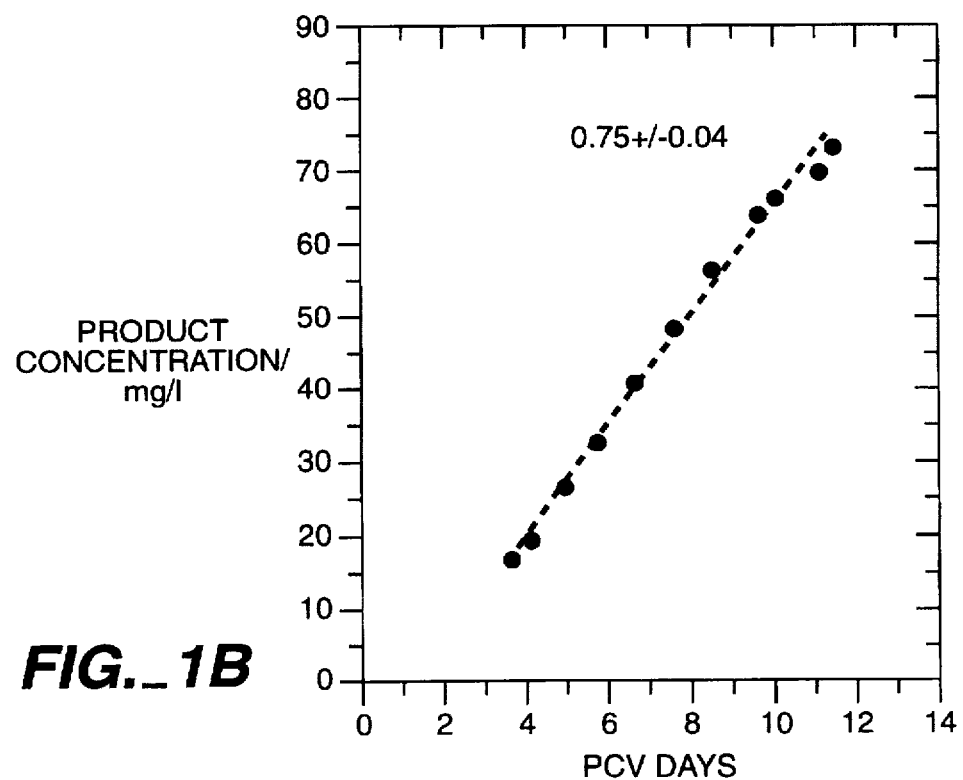
FIG._1B

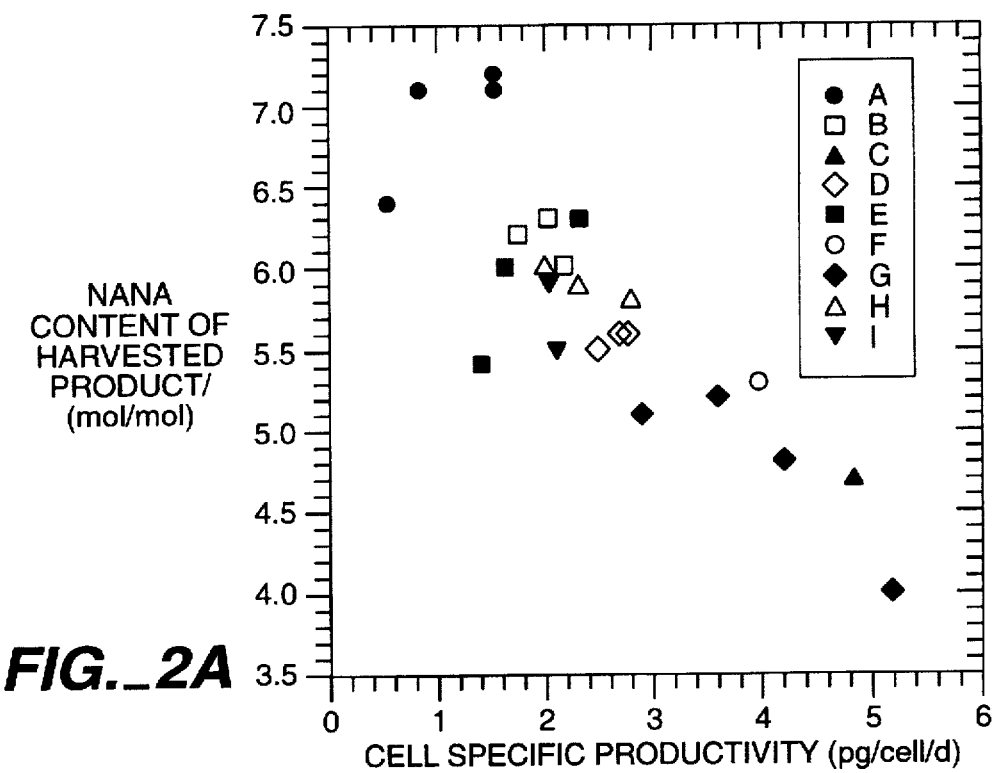
FIG._2A
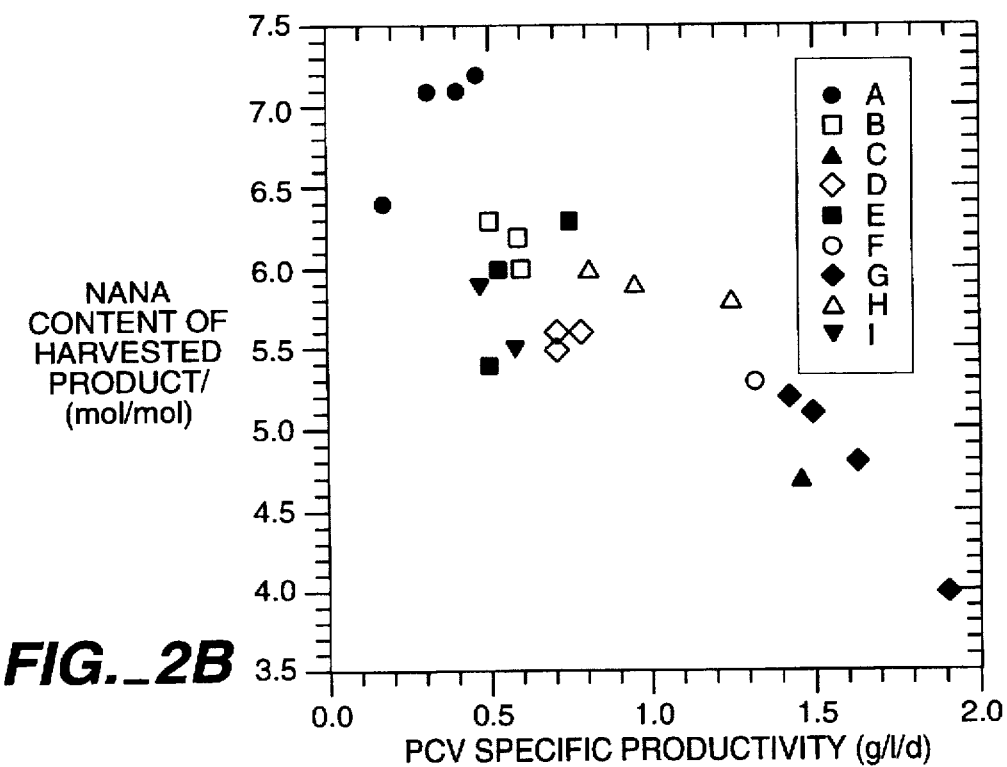
FIG._2B

MAMMALIAN CELL CULTURE PROCESS

FIELD OF THE INVENTION

This invention relates to processes for controlling the sialic acid content of glycoproteins produced in mammalian cell culture. The invention provides processes for increasing and decreasing the sialic acid content of glycoproteins produced by mammalian cell culture. The invention further relates to processes for producing tumor necrosis factor receptor (TNFR)-immunoglobulin (Ig) chimeras as well as novel TNFR1-IgG$_1$ preparations and their uses in the diagnosis and treatment of various inflammatory and immune disorders.

DESCRIPTION OF RELATED ART

Differences in glycosylation patterns of recombinantly produced glycoproteins have recently been the topic of much attention in the scientific community as recombinant proteins produced as probable prophylactics and therapeutics approach the clinic. The oligosaccharide side chains of the glycoproteins affect the protein's function (Wittwer A., and Howard, S. C. (1990) Biochem. 29:4175–4180) and the intramolecular interaction between portions of the glycoprotein resulting in the conformation and presented three dimensional surface of the glycoprotein (Hart, (1992) Curr. Op. Cell Biol., 4:1017–1023; Goochee, et al., (1991) Bio/Technology, 9:1347–1355; Parekh, R. B., (1991) Curr. Op. Struct. Biol., 1:750–754). Oligosaccharides may also serve to target a given polypeptide to certain structures based upon specific cellular carbohydrate receptors (Bevilacqua, M. P. and Nelson, R. M., (1993) J. Clin. Invest. 91:379–387; Nelson, R. M., et al., (1993) J. Clin. Invest. 91:1157–1166, Norgard, K. E. et al., (1993) Proc. Natl. Acad. Sci. USA 90:1068–1072; Imai, Y. et al., (1993) Nature 361:555–557). The terminal sialic acid component of the glycoprotein oligosaccharide side chain affects absorption, serum half life, and clearance from the serum, as well as the physical, chemical and immunogenic properties of the glycoprotein (Parekh, R. B., supra; Varki, A., (1993) Glycobiology 3:97–100; Paulson, J. (1989), TIBS, 14:272–276; Goochee, et al., (1991) Biotechnology 9:1347–1355; Kobata, A, (1992) Eur. J. Biochem. 209:483–501). It is therefore important to maintain the sialic acid content of glycoproteins, particularly of those proteins intended for use as therapeutics.

Much attention has been paid to the factors which affect glycosylation during recombinant protein production such as growth mode (adherent or suspension), fetal bovine serum in media formulation, culture density, oxygenation, pH, purification schemes and the like (Werner, R. and Noe, W. (1993), Drug Res. 43:1134–1249; Hayter et al., (1992) Biotech. and Bioeng. 39:327–335; Borys et al., (1994) Biotech and Bioeng. 43:505–514; Borys et al., (1993) Bio/technology 11:720–724; Hearing et al., (1989) J. Cell Biol. 108:339–353; Goochee et al., in Frontiers in Bioprocessing II, Todd et al., eds (1992) American Chemical Society pp.199–240; U.S. Pat. No. 5,096,816; Chotigeat, W., (1994) Cytotech. 15:217–221). Several groups have investigated the process parameters that surround the production of recombinant proteins and especially the effect of media composition in the production of recombinant proteins (Park et al., (1992) Biotech. Bioeng. 40:686–696; Cox and McClure, (1983) In Vitro, 19:1–6; Mizutani et al., (1992) Biochem. Biophys. Res. Comm. 187:664–669; Le Gros et al., (1985) Lymph. Res. 4(3):221–227).

Addition of alkanoic acids such as butyric acid are known to effect the transient expression of foreign DNA in recombinant cell culture (Prasad, and Sinha, (1976) In Vitro, 12:125–132; Japanese Patent Application No. 62-48935; Japanese Patent Application No. 55-150440; Klehr et al., (1992) Biochem. 31:3222–3229; Gorman, and Howard, (1983) Nucleic acid Res. 11:7631–7648). However, sodium butyrate has a range of effects on gene expression across various cell lines and media compositions (D'Anna et al., (1980) Biochem. 19:2656–2671; Hagopian, H. K., (1977) Cell 12:855–860) and protein production (Milhaud (1980) J. Cell. Physiol. 104:163–170; U.K. Patent Application No. GB 2 122 207 A) suggesting that butyrate may modify gene expression (Yuan et al., (1985) J. Biol. Chem. 3778–3783) or inhibit the expression of certain genes (Yuan et al., supra).

European Patent No. 0 239 292 B1 describes a process for the enhanced production of protein in the presence of an alkanoic acid or a salt thereof such as butyric acid. The publication, however, provides little guidance in selecting appropriate concentrations of the additive and further does not address the effect of the additive on protein glycosylation. Others have described that the addition of low levels (0–1.5 mM) of sodium butyrate to cell culture production medium to increase cell specific productivity leads to concomitant increases in acidic glycoforms (corresponding to increased sialic acid content) of the recombinant protein produced (Chotigeat, et al., (1994) Cytotech. 15:217–221).

Several groups have looked at the effects of osmolality on cell growth and polypeptide production (Ozturk and Palsson (1991) Biotech. and Bioeng. 37:989–993; Stubblefield et al., (1960) Cancer Research, 20:1646–1655; Garcia-Perez et al., (1989) Journal of Biological Chemistry, 264(28):16815–16821; Miner et al., (1981) Invasion Metastasis, 1:158–174; GB 2,251,249; EP 481,791; U.S. Pat. No. 5,151, 359; U.S. Pat. No. 4,724,206; U.S. Pat. No. 5,122,469; and WO 89/04867). Various osmolality ranges for cell growth or polypeptide production have been proposed. Generally, the osmolality of the cell culture medium is increased via the addition of NaCl or amino acids. Environmental stresses such as increased salt concentrations lead, in some instances, to increased cell product production. The notion that increased expression of mammalian protein products can be achieved in mammalian cell cultures through solute stress, e.g., the addition of salt, lactic acid, ammonia to the culture media has been reported (International Publication No. WO 89/04867) These stresses are generally growth inhibitory but favor cell specific productivity.

Others have discussed the effect of glucose concentration on cell growth and/or polypeptide production in recombinant cell culture. See, for example, Park et al., (1992) Biotechnology and Bioengineering, 40:686–696; Huang et al., (1991) Journal of Biotechnology, 18:161–162; EP 387, 840; Reuveny et al., (1986) Journal of Immunological Methods, 86:53–59; Fine et al., (1976) In Vitro, 12(10):693–701; Dircks et al., (1987) Exp. Eye Res., 44:951–958; Mizutani et al., (1992) Biochemical and Biophysical Research Communications, 187(2):664–669; Sugiura, (1992) Biotechnology and Bioengineering, 39:953–959; WO 88/01643; Graf et al., (1989) DECHEMA Biotechnol. Conf., 3:615–618; Japanese Patent Application No. JP 1-101882; U.S. Pat. No. 3,926,723; WO 87/00195; and Fleischaker, Jr., Ph.D. Thesis, Massachusetts Institute of Technology, pp. 196–229 (June 1982). However, the previous studies have not studied the effect of various process parameters on the sialic acid content of the mature protein, a factor in glycoprotein production that is tantamount to clinical success.

The present invention provides for processes for controlling the content of sialic acid of glycoproteins produced by mammalian cell culture.

SUMMARY OF THE INVENTION

The present inventors have discovered that certain mammalian cell culture process parameters affect cell specific productivity as well as the extent and type of glycosylation of the proteins produced. More particularly, the present inventors have found that certain factors which enhance cell specific productivity have an inverse effect on the sialic acid content of the produced protein. The present inventors have therefore devised various cell culture processes to enrich particular glycoforms of glycoproteins produced in mammalian cell culture.

Accordingly, the invention provides for a process for controlling the sialic acid content of a glycoprotein produced by mammalian cell culture. According to this aspect of the invention, varying the production rate of the glycoprotein in the production phase of the cell culture leads to variations in the sialic acid content of the mature glycoprotein. More particularly, an increase in cell specific productivity during the glycoprotein production phase results in a decrease in sialic acid content of the mature protein. Conversely, a decrease in cell specific productivity results in an increase in sialic acid content in the mature protein.

The present invention provides, in a particular embodiment, for varying the cell specific productivity of a mammalian host cell during the protein production phase of mammalian cell culture by controlling factors which affect cell specific productivity. According to one aspect of the invention, the concentration of factors which enhance DNA transcription are controlled. In another embodiment cell specific productivity is controlled by maintaining the osmolality of the cell culture within certain margins. According to the invention, any of the foregoing parameters are controlled, alone or in combination, to affect the mature glycoprotein sialic acid content.

In a particular embodiment of the present invention, the factor which enhances DNA transcription is an alkanoic acid or salt thereof such as sodium butyrate at a concentration of about 0.1 mM to about 20 mM. According to a second aspect of the invention, the osmolality of the cell culture is maintained between about 250–600 mOsm. In a further aspect, the temperature of the cell culture is controlled between about 30° C. and 37° C.

In a preferred embodiment, the invention provides for a process for increasing the sialic acid content of the mature glycoprotein produced by mammalian cell culture comprising maintaining a lower cell specific productivity by controlling any or all of the above identified process parameters, optionally together with other parameters known in the art. According to this aspect of the present invention, culturing the host cell at a concentration of the alkanoic acid or salt thereof of about 0.1 mM to about 6 mM, and optionally together with maintaining the osmolality of the cell culture at about 300–450 mOsm produces a protein with an increased sialic acid content.

In a further preferred embodiment, the invention provides for a process for decreasing the sialic acid content of the mature glycoprotein produced by mammalian cell culture comprising increasing cell specific productivity of the cell culture. The cell specific productivity is increased, in a preferred embodiment, by providing a cell culture process which comprises any of, culturing the host cell at a concentration of an alkanoic acid or salt thereof of about 6 mM to about 12 mM; and, maintaining the osmolality of the cell culture at about 450–600 mOsm.

The invention further provides, in a particular embodiment, for a cell culture process with three phases of cell culture. The invention therefore provides a process for controlling the sialic acid content of a glycoprotein produced by mammalian cell culture comprising the steps of culturing a host cell which expresses the protein in a growth phase for a period of time and under such conditions that cell growth is maximized. According to this aspect of the present invention, the growth phase is followed by a transition phase in which cell culture parameters for the desired sialic acid content of the mature glycoprotein are selected and engaged. The transition phase is followed by a production phase of the cell culture wherein parameters selected in the transition phase are maintained and glycoprotein product is produced and harvested. Varying the cell specific productivity of the production phase of the cell culture by adding an alkanoic acid or a salt thereof to the cell culture at a concentration of about 0.1 mM to about 20 mM and engaging an osmolality of the cell culture at about between 250 and 600 mOsm, optionally in combination with one another during the transition phase produces a protein with differing amounts of sialic acid.

In a further preferred embodiment, the present invention provides a process for controlling the amount of sialic acid present in a soluble type 1 tumor necrosis factor receptor (TNFR1)-immunoglobulin $G_1$ ($IgG_1$) chimeric protein. The present inventors have discovered that, under certain conditions of production, novel TNFR1-$IgG_1$ glycoform preparations may be obtained which exhibit the desirable properties of prolonged clearance from the blood while retaining significant functional activity. A long functional half-life permits simplified, bolus-dose administration and contributes to in vivo potency of the glycoprotein produced allowing for lower dose forms of the glycoprotein.

According to this aspect of the present invention, a TNFR1-$IgG_1$ glycoprotein molecule is produced that contains increased sialic acid residues. The cell culture parameters for the production phase of the TNFR1-$IgG_1$ are selected to obtain the desired sialic acid content. In a preferred embodiment, the sodium butyrate is present in the production phase at a concentration of about 0.1 to about 6 mM and the osmolality is maintained at about 300–450 mOsm. In a more preferred aspect the sodium butyrate concentration is about 1 mM and the osmolality is maintained at about 350–400 mOsm.

In yet another embodiment, the present invention provides for a preparation of TNFR1-$IgG_1$ glycoprotein produced by the process of the present invention. According to this aspect of the invention a preparation is provided comprising TNFR1-$IgG_1$ in which the range of pI of the preparation is between about 5.5 and 7.5. Further provided is a TNFR1-$IgG_1$ preparation having a molar ratio of sialic acid to protein of about 4 to about 7 and especially about 5 to about 6. In yet another aspect, the TNFR1-IgG1 preparation has about 1 to about 2 moles of exposed N-acetylglucosamine residues per mole of protein. In a further aspect, the preparation has a molar ratio of sialic acid to N-acetylglucosamine of about 0.35 to about 0.5 and more preferably about 0.4 to about 0.45.

The present invention also provides a therapeutic composition comprising the above preparation useful in the treatment of TNF-mediated pathologic conditions.

DESCRIPTION OF THE DRAWINGS

FIG. 1A and FIG. 1B. FIGS. 1A and 1B show the method used to calculate specific productivity of a typical cell culture process in the production phase. The specific productivity can be expressed as a function of the viable cell counts (viable cell days) as shown in FIG. 1A; or packed cell volume (PCV) as shown in FIG. 1B. The specific production rate is given with the range for a 90% confidence interval.

FIG. 2A and FIG. 2B. FIGS. 2A and 2B show the correlation between specific productivity based on viable cell days (FIG. 2A) and packed cell volume (PCV) (FIG. 2B) during the production phase and the sialic acid (NANA) content of the harvested product. Values for 9 different processes (A-I) are shown. The data points represent independent production processes as described in Table I.

DETAILED DESCRIPTION OF THE INVENTION

I. Definitions

The carbohydrate moieties of the present invention will be described with reference to commonly used nomenclature for the description of oligosaccharides. A review of carbohydrate chemistry which uses this nomenclature is found in Hubbard and Ivatt (1981) Ann., Rev. Biochem. 50:555–583. This nomenclature includes, for instance, Man, which represents mannose; GlcNAc, which represents 2-N-acetylglucosamine; Gal which represents galactose; and Glc, which represents glucose. Sialic acids are described with reference to the shorthand notation NeuNAc, for 5-N-acetylneuraminic acid, and NeuNGc for 5-glycolylneuraminic acid (J. Biol. Chem, 1982 257:3347; J. Biol. Chem., 1982, 257:3352).

"Osmolality" is a measure of the osmotic pressure of dissolved solute particles in an aqueous solution. The solute particles include both ions and non-ionized molecules. Osmolality is expressed as the concentration of osmotically active particles (i.e., osmoles) dissolved in 1 kg of solution (1 mOsm/kg $H_2O$ at 38° C. is equivalent to an osmotic pressure of 19 mm Hg). "Osmolarity," by contrast, refers to the number of solute particles dissolved in 1 liter of solution. When used herein, the abbreviation "mOsm" means "milliosmoles/kg solution".

As used herein, "glycoprotein" refers generally to peptides and proteins having more than about ten amino acids and at least one oligosaccharide side chain. The glycoproteins may be homologous to the host cell, or preferably, they are heterologous, i.e., foreign, to the host cell being utilized, such as a human protein produced by a Chinese hamster ovary cell. Preferably, mammalian glycoproteins (glycoproteins that were originally derived from a mammalian organism) are used, more preferably, those which are directly secreted into the medium. Examples of mammalian glycoproteins include molecules such as cytokines and their receptors, as well as chimeric proteins comprising cytokines or their receptors, including, for instance tumor necrosis factor alpha and beta, their receptors (TNFR-1; EP 417,563 published 20 Mar. 1991; and TNFR-2, EP 417,014 published 20 Mar. 1991) and their derivatives; renin; a growth hormone, including human growth hormone, and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; chimeric proteins, such as immunoadhesins, and fragments of any of the above-listed polypeptides.

The terms "cell culture medium" and "culture medium" refer to a nutrient solution used for growing mammalian cells that typically provides at least one component from one or more of the following categories:

1) an energy source, usually in the form of a carbohydrate such as glucose;

2) all essential amino acids, and usually the basic set of twenty amino acids plus cysteine;

3) vitamins and/or other organic compounds required at low concentrations;

4) free fatty acids; and 5) trace elements, where trace elements are defined as inorganic compounds or naturally occurring elements that are typically required at very low concentrations, usually in the micromolar range.

The nutrient solution may optionally be supplemented with one or more components from any of the following categories:

1) hormones and other growth factors as, for example, insulin, transferrin, and epidermal growth factor;

2) salts and buffers as, for example, calcium, magnesium, and phosphate;

3) nucleosides and bases such as, for example, adenosine, thymidine, and hypoxanthine; and 4) protein and tissue hydrolysates.

The term "mammalian host cell", "host cell", "mammalian cell" and the like, refer to cell lines derived from mammals that are capable of growth and survival when placed in either monolayer culture or in suspension culture in a medium containing the appropriate nutrients and growth factors. The necessary growth factors for a particular cell line are readily determined empirically without undue experimentation, as described for example in *Mammalian Cell Culture* (Mather, J. P. ed., Plenum Press, N.Y. [1984]), and Barnes and Sato, (1980) Cell, 22:649. Typically, the cells are capable of expressing and secreting large quantities of a particular glycoprotein of interest into the culture medium. Examples of suitable mammalian host cells within the context of the present invention may include Chinese hamster ovary cells/-DHFR (CHO, Urlaub and Chasin, Proc. Natl. Acad. Sci. USA, 77:4216 [1980]); dp12.CHO cells (EP 307,247 published 15 Mar. 1989); monkey kidney CV1 line transformed by SV40 (COS-7, ATCC CRL 1651); human embryonic kidney line (293 or 293 cells subcloned for growth in suspension culture, Graham et al., J. Gen Virol., 36:59 [1977]); baby hamster kidney cells (BHK, ATCC CCL 10); mouse sertoli cells (TM4, Mather, Biol. Reprod., 23:243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44–68 [1982]); MRC 5 cells; FS4 cells; and a human hepatoma line (Hep G2).

Preferred host cells include Chinese hamster ovary cells/ -DHFR (CHO, Urlaub and Chasin, Proc. Natl. Acad. Sci. USA, 77:4216 [1980]); dp12.CHO cells (EP 307,247 published 15 March 1989).

The term "peptone" within the context of the present invention is meant to refer to a media supplement that is essentially hydrolyzed animal protein. The source of this protein may be animal by-products from slaughter houses, purified gelatin, or plant material. The protein is typically hydrolyzed using acid, heat or various enzyme preparations. Preferred peptone mixtures are, for example, "Primatone RL" and "Primatone MS", both of which are commercially available (Sheffield, England).

"Cell specific productivity", "cell specific rate" and the like, are used herein to refer to the specific, i.e., per cell, or per measure of cell mass or volume, product expression rate. The cell specific productivity is measured in, for example, grams of protein produced per cell per day. Cell specific productivity can be conveniently measured according to the integral method:

$$dP/dt = q_p X, \text{ or}$$

$$P = q_p \int_0^t X dt$$

where $q_p$ is the cell specific productivity constant, X is the number of cells or cell volume, or cell mass equivalents, and dP/dt is the rate of protein production. Hence, $q_p$ can be obtained from a plot of product concentration versus time integral of viable cells ($\int_0^t X dt$ "viable cell days"). According to this formula, when the amount of glycoprotein product produced is plotted against the viable cell days the slope is equivalent to the cell specific rate. Viable cells can be determined by several measures, for example, biomass, $O_2$ uptake rate, lactase dehydrogenase (LDH), packed cell volume or turbidity.

"Growth phase" of the cell culture refers to the period of exponential cell growth (the log phase) where cells are generally rapidly dividing. During this phase, cells are cultured for a period of time, usually between 1–4 days, and under such conditions that cell growth is maximized. The determination of the growth cycle for the host cell can be determined for the particular host cell envisioned without undue experimentation. "Period of time and under such conditions that cell growth is maximized" and the like, refer to those culture conditions that, for a particular cell line, are determined to be optimal for cell growth and division. During the growth phase, cells are cultured in nutrient medium containing the necessary additives generally at about 30°–40° C., in a humidified, controlled atmosphere, such that optimal growth is achieved for the particular cell line. Cells are maintained in the growth phase for a period of about between one and four days, usually between two to three days.

"Transition phase" of the cell culture refers to the period of time during which culture conditions for the production phase are engaged. During the transition phase environmental factors such as temperature of the cell culture, medium osmolality and the like are shifted from growth conditions to production conditions.

"Production phase" of the cell culture refers to the period of time during which cell growth has plateaued. During the production phase, logarithmic cell growth has ended and protein production is primary. During this period of time the medium is generally supplemented to support continued protein production and to achieve the desired glycoprotein product.

The term "expression" or "expresses" are used herein to refer to transcription and translation occurring within a host cell. The level of expression of a product gene in a host cell may be determined on the basis of either the amount of corresponding mRNA that is present in the cell or the amount of the protein encoded by the product gene that is produced by the cell. For example, mRNA transcribed from a product gene is desirably quantitated by northern hybridization. Sambrook et al., Molecular Cloning: A Laboratory Manual, pp. 7.3–7.57 (Cold Spring Harbor Laboratory Press, 1989). Protein encoded by a product gene can be quantitated either by assaying for the biological activity of the protein or by employing assays that are independent of such activity, such as western blotting or radioimmunoassay using antibodies that are capable of reacting with the protein. Sambrook et al., Molecular Cloning: A Laboratory Manual, pp. 18.1–18.88 (Cold Spring Harbor Laboratory Press, 1989).

By alkanoic acid or salt thereof is meant a straight or branched chain, saturated or unsaturated, alkanoic acid or salt thereof. The alkanoic acid is generally from one to ten carbon atoms and is preferably from three to six carbon atoms. An exemplary alkanoic acid is butyric acid and the corresponding salt is sodium butyrate.

II. Cell Culture Procedures

The present inventors have discovered that factors which increase cell specific productivity during the production of a glycoprotein produced by mammalian cell culture have an inverse effect on sialic acid content of the glycoprotein produced. Since proteins expressing one or more sialic acid residues per complex oligosaccharide structure have longer clearance rates in vivo the clearance rate of the glycoprotein produced may be manipulated within broad limits by the overall degree of sialylation of the preparation. The present invention provides for processes for controlling the extent of sialylation of a glycoprotein produced by mammalian cell culture. Following the methodology set forth herein, one is able to determine the precise process parameters that provide for the desired sialic acid content of a glycoprotein produced by mammalian cell culture.

According to the present invention a mammalian host cell is cultured to produce a recoverable glycoprotein product. The overall content of sialic acid in the glycoprotein is controlled by controlling cell culture parameters which affect cell specific productivity. Factors which affect cell specific productivity are well known in the art and include, but are not limited to, factors which affect DNA/RNA copy number, factors which affect RNA, such as factors which stabilize RNA, media nutrients and other supplements, the concentration of transcription enhancers, the osmolality of the culture environment, the temperature and pH of the cell culture, and the like. According to the adjustment invention adjustment of these factors, alone or in combination, to increase cell specific productivity generates a protein with a decreased sialic acid content. The adjustment of these factors, alone or in combination, to decrease cell specific productivity, generates a mature glycoprotein with an increased sialic acid content.

The invention will now be described with reference to various, including well known, cell culture techniques and principles.

According to the present invention mammalian cells are cultured to produce a desired glycoprotein product. In choosing a host cell for the production of the glycoprotein within the context of the present invention, it is important to recognize that different host cells have characteristic and specific mechanisms for the translational and post-translational processing and modification (e.g., glycosylation, cleavage) of the proteins expressed. Appropriate cell lines should be chosen to ensure that the desired post translational modifications are possible. Alternatively, host cells can be modified to express a desired gene product required for the specific post-translational modification.

In particular, the mammalian cells which express the desired protein should express or be manipulated to express the particular enzymes such that under the appropriate conditions, described herein, the appropriate post translational modification occurs in vivo. The enzymes include those enzymes necessary for the addition and completion of N- and O- linked carbohydrates such as those described in Hubbard and Ivan supra for N-linked oligosaccharides. The enzymes optionally include oligosaccharyltransferase, alpha-glucosidase I, alpha-glucosidase II, ER alpha(1,2) mannosidase, Golgi alpha-mannodase I, N-acetylglucosaminyltransferase I, Golgi alpha-mannodase II, N-acetylglucosaminyltransferase II, alpha (1,6)fucosyltransferase, and β(1,4)galactosyltranferase. Additionally, the host cell expresses the appropriate sialyl transferase that can be expected to attach the terminal sialic acid in specific position and linkage as part of the host cell genome. Optionally, the host cell can be made to express the appropriate sialyl transferases by, for instance, transfection of the host cell with the DNA encoding the sialyl transferase.

The sialyl transferases described above would be expected to add the terminal sialic acid residue to the appropriate oligosaccharide core structure such as Galβ1-4GlcNAc. Appropriate sialyl transferases within the context of the present invention include, but are not limited to, those sialyl transferases which catalyze the complex sialylation and branching of the N- and O-linked oligosaccharides.

For the culture of the mammalian cells expressing the desired protein and capable of adding the desired carbohydrates in specific position and linkage, numerous culture conditions can be used paying particular attention to the host cell being cultured. Suitable culture conditions for mammalian cells are well known in the art (J. Immunol. Methods (1983)56:221-234) or can be easily determined by the skilled artisan (see, for example, *Animal Cell Culture: A Practical Approach* 2nd Ed., Rickwood, D. and Hames, B. D., eds. Oxford University Press, New York (1992)), and vary according to the particular host cell selected.

The mammalian cell culture of the present invention is prepared in a medium suitable for the particular cell being cultured. Commercially available media such as Ham's F10 (Sigma), Minimal Essential Medium ([MEM], Sigma), RPMI-1640 (Sigma), and Dulbecco's Modified Eagle's Medium ([DMEM], Sigma) are exemplary nutrient solutions. In addition, any of the media described in Ham and Wallace,(1979) Meth. Enz., 58:44; Barnes and Sato,(1980) Anal. Biochem., 102:255; U.S. Pat. Nos. 4,767,704; 4,657, 866; 4,927,762; 5,122,469 or 4,560,655; International Publication Nos. WO 90/03430; and WO 87/00195; the disclosures of all of which are incorporated herein by reference, may be used as culture media. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range) lipids (such as linoleic or other fatty acids) and their suitable carriers, and glucose or an equivalent energy source. Any other necessary supplements may also be included at appropriate concentrations that would be known to those skilled in the art.

In a particular embodiment, the mammalian host cell is a CHO cell, preferably a dp12.CHO cell and a suitable medium contains a basal medium component such as a DMEM/HAM F-12 based formulation (for composition of DMEM and HAM F12 media, see culture media formulations in American Type Culture Collection Catalogue of Cell Lines and Hybridomas, Sixth Edition, 1988, pages 346–349) (the formulation of medium as described in U.S. Pat. No. 5,122,469 are particularly appropriate) with modified concentrations of some components such as amino acids, salts, sugar, and vitamins, and optionally containing glycine, hypoxanthine, and thymidine; recombinant human insulin, hydrolyzed peptone, such as Primatone HS or Primatone RL (Sheffield, England), or the equivalent; a cell protective agent, such as Pluronic F68 or the equivalent pluronic polyol; gentamycin; and trace elements.

The glycoproteins of the present invention may be produced by growing cells which express the desired protein under a variety of cell culture conditions. For instance, cell culture procedures for the large or small scale production of proteins are potentially useful within the context of the present invention. Procedures including, but not limited to, a fluidized bed bioreactor, hollow fiber bioreactor, roller bottle culture, or stirred tank bioreactor system may be used, in the later two systems, with or without microcarriers, and operated alternatively in a batch, fedbatch, or continuous mode.

In a preferred embodiment the cell culture of the present invention is performed in a stirred tank bioreactor system and a fed batch culture procedure is employed. In the preferred fed batch culture the mammalian host cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernate is not removed from the culturing vessel during the process (in perfusion culturing, the cells are restrained in the culture by, e.g., filtration, encapsulation, anchoring to microcarriers etc. and the culture medium is continuously or intermittently introduced and removed from the culturing vessel).

Further, the cells of the culture may be propagated according to any scheme or routine that may be suitable for the particular host cell and the particular production plan contemplated. Therefore, the present invention contemplates a single step or multiple step culture procedure. In a single step culture the host cells are inoculated into a culture environment and the processes of the instant invention are employed during a single production phase of the cell culture. Alternatively, a multi-stage culture is envisioned. In the multi-stage culture cells may be cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture.

According to a preferred aspect of the invention, fed batch or continuous cell culture conditions are devised to enhance growth of the mammalian cells in the growth phase of the cell culture. In the growth phase cells are grown under conditions and for a period of time that is maximized for growth. Culture conditions, such as temperature, pH, dissolved oxygen ($dO_2$) and the like, are those used with the particular host and will be apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30° to 38° C. and a suitable $dO_2$ is between 5–90% of air saturation.

At a particular stage the cells may be used to inoculate a production phase or step of the cell culture. Alternatively, as described above the production phase or step may be continuous with the inoculation or growth phase or step.

According to the present invention, the cell culture environment during the production phase of the cell culture is controlled. According to the process of the present invention, factors affecting cell specific productivity of the mammalian host cell are manipulated such that the desired sialic acid content is achieved in the resulting glycoprotein. In particular, factors which increase cell specific productivity are controlled during the production phase of the cell culture process such that the resulting glycoprotein product contains the desired sialic acid content.

In a preferred aspect, the production phase of the cell culture process is preceded by a transition phase of the cell culture in which parameters for the production phase of the cell culture are engaged.

According to one aspect of the present invention the concentration of a transcription enhancer such as an alkanoic acid, is manipulated to affect cell specific productivity and therefore the resulting sialic acid content of the mammalian cell glycoprotein product. The alkanoic acid may be any one of a number of single or branched chain alkanoic acids that enhance transcription of mammalian proteins. In a preferred embodiment the alkanoic acid is butyric acid and especially the salt thereof, sodium butyrate.

According to the present invention the concentration of sodium butyrate is controlled to control the cell specific productivity. Concentrations of sodium butyrate of between 0.1 and 20 mM are used and modified according to the particular host cell being cultured and the desired sialic acid content of the glycoprotein produced. In order to generate a protein with the desired sialic acid content a concentration of sodium butyrate is chosen which provides for the highest cell specific productivity with the most acceptable sialic acid profile. Therefore, according to the present invention concentrations of a transcription enhancer such as sodium butyrate are chosen to obtain the desired sialic acid content.

To increase sialic acid content of the mature glycoprotein, generally, lower concentrations of the transcription enhancer are used. The lower concentration provides for enhanced transcription, but maintains lower cell specific productivity while maintaining the viability of the host cell culture. Generally concentrations of the transcription enhancer such as sodium butyrate between about 0.1 mM and about 8 mM are used. More preferably concentrations between about 1.0 and 6.0 mM are used. In a particular embodiment about 6 mM sodium butyrate is used. In another embodiment about 1 mM sodium butyrate is used.

In another embodiment a glycoprotein is produced with a decreased level of sialic acid. According to this aspect of the present invention, mammalian cells are cultured under conditions such that cell specific productivity is increased. According to this aspect of the present invention a concentration of alkanoic acid or other appropriate transcription enhancer is chosen such that increased cell specific productivity generates a protein with the desired sialic acid profile. In a preferred embodiment the concentration of the alkanoic acid or salt thereof is between about 5 and 20 mM and more preferably between about 6 mM and 12 mM. In a particular embodiment, the concentration of sodium butyrate is about 12 mM.

In determining the appropriate concentration of the transcription enhancer such as an alkanoic acid or salt thereof, reference can be made to FIG. 2 as well as Table I infra at Example I. According to the present invention lower butyrate concentrations generally result in lower cell specific productivity. According to the invention concentrations of sodium butyrate are chosen keeping in mind other process parameters such as the osmolality of the production phase. As discussed below the osmolality can affect the cell specific productivity. Concentrations of butyrate are chosen keeping in mind the particular osmolality to be maintained during the production phase.

Alternatively, for other mammalian host cells and other glycoproteins, small test cultures can be prepared and rate of glycoprotein product production, i.e. the cell specific productivity can be determined and the resulting sialic acid content can be used to prepare a similar table and figure appropriate for the particular host cell being cultured, keeping in mind that decreases in cell specific productivity lead to increases in the sialic acid content of the glycoprotein produced. The alkanoic acid or salt thereof, such as sodium butyrate, or other appropriate transcription enhancer is added to the host cell culture at or about the time the production phase of the cell culture is initiated. Conveniently, a transition phase is employed during the cell culture process preceding the production phase in which the cell culture conditions as discussed herein are engaged for the desired cell specific productivity and hence the desired glycoform profile.

The alkanoic acid or salt thereof is added by any means known in the art. In a preferred embodiment the sodium butyrate is added in batch to the fed batch culture system with or without other appropriate nutrients as described herein or known to those skilled in the art of mammalian cell culture.

According to the instant invention the osmolality of the cell culture environment is controlled in addition to the factors noted above to regulate the extent of sialylation of the mature glycoprotein. In one embodiment, osmolality is controlled to control the sialic acid content of the mature protein independent of other factors which affect cell specific productivity. In another embodiment osmolality is controlled in addition to controlling other factors which affect cell specific productivity. In a preferred embodiment both osmolality and the concentration of alkanoic acid are controlled.

The osmolality of the cell culture environment is controlled to produce the desired balance between the cell specific productivity and the sialic acid profile of the resulting glycoprotein. Generally, cell specific productivity is increased when osmolality is increased. An osmolality which produces a protein with the desired sialic acid is chosen keeping in mind that increases in the osmolality generally lead to increase in production rate of the particular protein. In order to decrease the production rate and increase the sialic acid content of the mature glycoprotein osmolality is generally maintained at a lower level for the particular cell type being cultured.

For mammalian cell culture the osmolality of the culture medium is generally about 290–330 mOsm. However, increases in the osmolality generally lead to increase in production rate of proteins. An osmolality is chosen such that the production rate corresponds with the desired product profile. To increase the sialic acid content, production rate is decreased and osmolality is generally maintained within a lower margin keeping in mind the particular host cell being cultured. Osmolality in the range from about 250 mOsm to about 450 mOsm is appropriate for an increased sialic acid content. More preferably, the osmolality is maintained at about between 300 and 450 mOsm, according to this aspect of the invention, and more preferably between about 350 and 400 mOsm, and most preferably about 400 mOsm.

For a lower sialic acid content, an osmolality which provides an increased production rate is chosen. According to this aspect of the invention, the osmolality is maintained at about between 350–600 mOsm. and is preferably between about 450–550 mOsm. according to this aspect of the invention.

The skilled practitioner will recognize that media osmolality is dependent upon the concentration of osmotically active particles in the culture fluid and that a number of variables that make up a complex mammalian cell culture medium impact osmolality. The initial osmolality of the culture medium is determined by the composition of the culture medium. The osmolality can be measured using an osmometer such as that sold by Fisher Scientific, Pittsburgh, Pa., under the brand name OSMETTE (or the Osmette model 2007, available from Precision Systems, Inc. Natick Mass.), for example. In order to achieve an osmolality in the desired range, the concentration of various constituents in the culture medium can be adjusted.

Solutes which can be added to the culture medium so as to increase the osmolality thereof include proteins, peptides, amino acids, hydrolyzed animal proteins such as peptones, non-metabolized polymers, vitamins, ions, salts, sugars, metabolites, organic acids, lipids, and the like. In one embodiment, the osmolality is controlled by the addition of a peptone to the cell culture along with other components of the culture medium during a fed batch culture procedure.

According to the present invention the osmolality is maintained or adjusted to the desired range via the addition of for instance, a basal medium formulation including amino acids, various salts (e.g. NaCl), in addition to a peptone. In a preferred embodiment, the culture medium is supplemented with, for instance, a basal culture medium containing excess amino acids (see, e.g., the "Super" medium of U.S. Pat. No. 5,122,469), glucose, and a peptone.

It will be appreciated however, that the concentration(s) of other constituents in the culture medium can be modified in order to achieve an osmolality range as set forth above. By controlling either intermittently or continuously the concentration of glucose (the primary energy source), for instance, in the culture medium throughout the culturing, the osmolality of the medium can be maintained at about the desirable range specified. Controlling the glucose concentration serves to provide adequate carbon source to the cells and simultaneously control the production of lactic acid by the host cells. This is advantageous in that it limits the pH decrease in the culture medium which necessitates the addition of a neutralizer (e.g., a base such as $Na_2CO_3$ or NaOH), which causes the osmolality to rise.

The medium can be supplemented to maintain the osmolality within the appropriate margins according to whatever scheme is being used to maintain the cell culture. In a preferred embodiment, the culture system is a fed batch culture system and the medium is supplemented in batch in a feed during the production phase of the cell culture. Additionally the medium can be supplemented during the production phase as described infra.

Alternatively, intermittent off-line sampling of the culture medium can be carried out. The osmolality of the culture medium can then be modified by the modulation of a feed solution as required.

It will be understood by the skilled artisan that the cell culture procedures of the present invention are selected to achieve the desired level of sialylation of the produced protein. Process parameters in addition to those described herein which influence the degree of sialylation include oxygen level, and glucose level. Culture density, time and storage conditions such as temperature also influence sialylation. The present invention is meant to include those process parameters which are additionally most suitable for enhanced sialylation.

III. Recovery of the Glycoprotein

Following the polypeptide production phase, the polypeptide of interest is recovered from the culture medium using techniques which are well established in the art.

The polypeptide of interest preferably is recovered from the culture medium as a secreted polypeptide, although it also may be recovered from host cell lysates.

As a first step, the culture medium or lysate is centrifuged to remove particulate cell debris. The polypeptide thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG. A protease inhibitor such as phenyl methyl sulfonyl fluoride (PMSF) also may be useful to inhibit proteolytic degradation during purification. One skilled in the art will appreciate that purification methods suitable for the polypeptide of interest may require modification to account for changes in the character of the polypeptide upon expression in recombinant cell culture.

Especially preferred within the context of the present invention are purification techniques and processes which select for the carbohydrates of the invention. The desired glycoforms of the present invention may be enriched for sialic acid-containing molecules by, for example, ion-exchange soft gel chromatography or HPLC using cation- or anion-exchange resins, wherein the more acidic fraction is collected.

IV. Analysis of the Glycoprotein

The complex carbohydrate portion of the glycoprotein produced by the processes of the present invention may be readily analyzed if desired, by conventional techniques of carbohydrate analysis. Thus, for example, techniques such as lectin blotting, well-known in the art, reveal proportions of terminal mannose or other sugars such as galactose. Termination of mono-, bi-, tri-, or tetra-antennary oligosaccharide by sialic acids can be confirmed by release of sugars from the protein using anhydrous hydrazine or enzymatic methods and fractionation of oligosaccharides by ion-exchange or size exclusion chromatography or other methods well-known in the art. The pI of the glycoprotein can also be measured, before and after treatment with neuraminidase to remove sialic acids. An increase in pI following neuraminidase treatment indicates the presence of sialic acids on the glycoprotein.

The carbohydrate structures of the present invention occur on the protein expressed as N-linked or O-linked carbohydrates. The N-linked and O-linked carbohydrates differ primarily in their core structures. N-linked glycosylation refers to the attachment of the carbohydrate moiety via GlcNAc to an asparagine residue in the peptide chain. The N-linked carbohydrates all contain a common Man1-6(Man1-3)Manβ1-4GlcNAcβ1-4GlcNAcβ-R core structure. Therefore, in the core structure described, R represents an asparagine residue of the produced protein. The peptide sequence of the protein produced will contain an asparagine-X-serine, asparagine-X-threonine, and asparagine-X-cysteine, wherein X is any amino acid except proline. O-linked carbohydrates, by contrast are characterized by a common core structure, which is the GalNAc attached to the hydroxyl group of a threonine or serine. Of the N-linked, and O-linked carbohydrates, the most important are the complex N- and O-linked carbohydrates. Such complex carbohydrates will contain several antenanary structures. The mono-, bi-, tri,-, and tetra-, outer structures are important for the addition of terminal sialic acids. Such outer chain structures provide for additional sites for the specific sugars and linkages that comprise the carbohydrates of the instant invention.

The resulting carbohydrates can be analyzed by any method known in the art including those methods described herein. Several methods are known in the art for glycosylation analysis and are useful in the context of the present invention. Such methods provide information regarding the identity and the composition of the oligosaccharide attached to the peptide. Methods for carbohydrate analysis useful in the present invention include but are not limited to lectin chromatography; HPAEC-PAD, which uses high pH anion exchange chromatography to separate oligosaccharides based on charge; NMR; Mass spectrometry; HPLC; GPC; monosaccharide compositional analysis; sequential enzymatic digestion.

Additionally, methods for releasing oligosaccharides are known. These methods include 1)enzymatic, which is commonly performed using peptide-N-glycosidase F/endo-β-galactosidase; 2) β elimination using harsh alkaline environment to release mainly O-linked structures; and 3) chemical methods using anhydrous hydrazine to release both N-and O-linked oligosaccharides Analysis can be performed using the following steps:

1. Dialysis of the sample against deionized water, to remove all buffer salts, followed by lyophilization.
2. Release of intact oligosaccharide chains with anhydrous hydrazine.
3. Treatment of the intact oligosaccharide chains with anhydrous methanolic HCl to liberate individual monosaccharides as O-methyl derivative.
4. N-acetylation of any primary amino groups.
5. Derivatization to give per-O-trimethylsilyl methyl glycosides.
6. Separation of these derivative, by capillary GLC (gas—liquid chromatography) on a CP-SIL8 column.
7. Identification of individual glycoside derivatives by retention time from the GLC and mass spectroscopy, compared to known standards.
8. Quantitation of individual derivatives by FID with an internal standard (13-O-methyl-D-glucose).

Neutral and amino-sugars can be determined by high performance anion-exchange chromatography combined with pulsed amperometric detection (HPAE-PAD Carbohydrate System, Dionex Corp.). For instance, sugars can be released by hydrolysis in 20% (v/v) trifluoroacetic acid at 100° C. for 6 h. Hydrolysates are then dried by lyophilization or with a Speed-Vac (Savant Instruments). Residues are then dissolved in 1% sodium acetate trihydrate solution and analyzed on a HPLC-AS6 column as described by Anumula et al. (Anal. Biochem. 195:269–280 (1991).

Sialic acid can be determined separately by the direct colorimetric method of Yao et al. (Anal Biochem. 179:332–335 (1989)) in triplicate samples. In a preferred embodiment the thiobarbaturic acid (TBA) of Warren, L. J. Biol Chem 238:(8) (1959) is used.

Alternatively, immunoblot carbohydrate analysis may be performed. According to this procedure protein-bound carbohydrates are detected using a commercial glycan detection system (Boehringer) which is based on the oxidative immunoblot procedure described by Haselbeck and Hosel [Haselbeck et al. Glycoconjugate J., 7:63 (1990)]. The staining protocol recommended by the manufacturer is followed except that the protein is transferred to a polyvinylidene difluoride membrane instead of nitrocellulose membrane and the blocking buffers contained 5% bovine serum albumin in 10 mM tris buffer, pH 7.4 with 0.9% sodium chloride. Detection is made with anti-digoxigenin antibodies linked with an alkaline phosphate conjugate (Boehringer), 1:1000 dilution in tris buffered saline using the phosphatase substrates, 4-nitroblue tetrazolium chloride, 0.03% (w/v) and 5-bromo-4 chloro-3-indoyl-phosphate 0.03% (w/v) in 100 mM tris buffer, pH 9.5, containing 100 mM sodium chloride and 50 mM magnesium chloride. The protein bands containing carbohydrate are usually visualized in about 10 to 15 min.

The carbohydrate may also be analyzed by digestion with peptide-N-glycosidase F. According to this procedure the residue is suspended in 14 μl of a buffer containing 0.18% SDS, 18 mM beta-mercaptoethanol, 90 mM phosphate, 3.6 mM EDTA, at pH 8.6, and heated at 100 ° C. for 3 min. After cooling to room temperature, the sample is divided into two equal parts. One aliquot is not treated further and serves as a control. The second fraction is adjusted to about 1% NP-40 detergent followed by 0.2 units of peptide-N-glycosidase F (Boehringer). Both samples are warmed at 37° C. for 2 hr and then analyzed by SDS-polyacrylamide gel electrophoresis.

V. Tumor Necrosis Factor Receptor-Immunoglobulin Chimeras

In a preferred embodiment the processes of the present invention are used to produce tumor necrosis factor receptor (TNFR)-Immunogloblun (Ig) chimeras. Especially preferred among this class of chimeric proteins is the soluble type 1 TNFR IgG$_1$. The TNFR1-IgG$_1$ chimeras produced are useful in the treatment or diagnosis of many TNF-mediated or TNF-related diseases and disorders. The term "treatment" in this context includes both prophylactic (prevention), suppression (e.g., of a symptom) and treatment of an existing condition. The pathologic conditions associated with TNF include but are not limited to gram negative and gram positive bacteremia, endotoxic shock, graft rejection phenomena, rheumatoid arthritis, systemic lupus, Crohn's disease and other autoimmune and inflammatory diseases associated with TNF.

The TNFR1-IgG$_1$ preparations of the instant invention are useful generally in those indications where monoclonal antibodies to TNF have been found to be useful. For instance, in animal models, monoclonal antibodies to TNF-alpha were found to have protective effect when employed prophylactically (Tracey, K. J. et al., (1987) Nature 330:662). In a phase I clinical study reported by Exley, A. R. et al., (1990) Lancet 335:1275, a murine monoclonal antibody to recombinant human TNF-alpha was found to be safe when administered to human patients with severe septic shock. TNFR1-IgG$_1$ is suitably used in the treatment of rheumatoid arthritis as well as septic shock.

In a method of treating a disease or disorder associated with TNF a therapeutically active amount of TNFR1-IgG$_1$ preparation is administered to a subject in need of such treatment. The preferred subject is a human.

An effective amount of a TNFR1-IgG$_1$ glycoform preparation of the instant invention for the treatment of a disease or disorder is in the dose range of 0.01–100 mg/patient; preferably 1 mg-75 mg/patient and most preferably between about 10 and about 50 mg/patient.

For administration, the TNFR1-IgG$_1$ preparation should be formulated into an appropriate pharmaceutical or therapeutic composition. Such a composition typically contains a therapeutically active amount of the TNFR1-IgG$_1$ preparation and a pharmaceutically acceptable excipient or carrier such as saline, buffered saline, dextrose, or water. Compositions may also comprise specific stabilizing agents such as sugars, including mannose and mannitol, and local anesthetics for injectable compositions, including, for example, lidocaine.

The present invention provides compositions which further comprise a therapeutically active amount of an additional active ingredient such as monoclonal antibodies (e.g. anti-TNF antibodies, antibodies to Mac1 or LFA 1) or other receptors associated with TNF production, e.g. IL-1 or IL-2 receptors, etc.

A preferred therapeutic composition for single or combined therapy, as above, comprises a novel TNFR1-IgG$_1$ preparation of this invention which exhibits prolonged clearance from the blood while retaining significant functional activity. Such a prolonged functional half-life permits simplified, bolus-dose administration and contributes to potency in vivo. Preferred TNFR1-IgG$_1$ chimeras in the therapeutic composition include the TNFR1-IgG$_1$ and preparations described herein, for example:

(1) TNFR1-IgG$_1$ preparations comprising a complex oligosaccharide terminated by one or more residues of a sialic acid;

(2) TNFR1-IgG$_1$ preparations wherein the range of isoelectric point, pI, of the preparation is between 5.5 and 7.5 as determined by chromatofocusing, in which the pI is sensitive to neuraminidase treatment;

(3) TNFR1-IgG$_1$ preparations having about 1–2 moles of exposed N-acetylglucosamine residues per mole of protein.

(4) TNFR1-IgG$_1$ preparations having a molar ratio of sialic acid to protein of about 4–7, especially about 5–6.

(5) TNFR1-IgG$_1$ preparations having a molar ratio of sialic acid to N-acetylglucosamine of about 0.35 to about 0.5, and more preferably of about 0.4 to about 0.45.

Routes of administration for the individual or combined therapeutic compositions of the present invention include standard routes, such as, for example, intravenous infusion or bolus injection.

Also provided is the use of a TNFR1-IgG$_1$ preparation of this invention in the manufacture of a medicament for the treatment of a human or animal.

Having now generally described the invention, the same will be more readily understood through reference to the following examples which are provided by way of illustration, and are not intended to be limiting of the present invention, unless specified.

EXAMPLE I

The biological effects of TNF-alpha and TNF-beta are mediated through specific receptors (Dembic et al., (1990) Cytokines, 2:231). Molecular cloning has demonstrated the existence of two distinct types of TNF receptors (TNFR) with apparent molecular masses of 55 kD (type 1) (Schall et al., (1990) Cell 61:361) and 75 kD (type 2) (Smith et al., (1990) Science 248:1019), each of which naturally binds to both TNF alpha and TNF beta (Loetscher et al., (1990) Cell, 61:351; Shall et al. (1990) Cell, 61:361; Kohno et al., (1990) Proc. Natl. Acad. Sci. USA 87:8331). The extracellular portions of both receptors are found naturally as soluble TNF binding proteins (Kohno et al., supra). TNF agonists have been created which block the deleterious effect of TNF in various immune and inflammatory events (Peppel et al., (1991) J. Exp. Med., 174:1483–1489; Ulich (1993) Am. J. Path., 142:1335–1338; Howard, O. M. Z., (1993) Proc. Natl. Acad. Sci. USA 90:2335–2339; Wooley, P. H., (1993) J. Immunol. 151:6602–6607). One such agonist (Werner et al., (1991) J. Cell. Biochem. Abstracts, 20th annual meeting, p. 115) combines the extracellular domain of human 55 kD type 1 TNFR with a portion of the hinge and Fc regions of human immunoglobulin G1 heavy chain.

In this Example mammalian cells transfected with a vector containing the cDNA encoding the TNFR1-IgG$_1$ chimera were cultured.

Methods

A. Cell Line

The Chinese hamster ovary (CHO)cell line used as the mammalian host cell line was derived from CHO-K1 (ATCC No. CCL61 CHO-K1). A CHO-K1 mutant dihydrofolate reductase (DHFR$^-$) deficient cell line named CHO-K1 DUX-B11 (DHFR$^-$) (obtained from Dr. L. Chasin of Columbia University; Simonsen, C. C., and Levinson, A. D., (1983) Proc. Natl. Acad. Sci. USA 80:2495–2499; Urlaub G., and Chasin, L., (1980) Proc. Natl. Acad. Sci USA 77:4216–4220) was then used to obtain a cell line with a reduced requirement for insulin by transfection with the vector containing the cDNA for the preproinsulin (Sures et al., (1980) Science, 208:57–59). The selected clone designated dp12.CHO requires glycine, hypoxanthine, and thymidine for growth, thus verifying their DHFR$^-$ genotype.

B. Construction of Soluble Type 1 TNFR-IgG$_1$. Chimera

A soluble type 1 TNFR-IgG$_1$ chimera was constructed by gene fusion of the extracellular domain of human type 1 TNFR with the hinge region and C$_H$2 and C$_H$3 domains of IgG$_1$ heavy chain (further referred to as TNFR1-IgG$_1$).

The human type 1 TNFR encoding DNA sequence (see Loetscher et al., Supra) was obtained from the plasmid pRK-TNF-R [Schall et al., Cell 61, 361 (1990)]. To construct this starting plasmid, a 2.1 kb placental cDNA clone (Schall et al., Supra) was inserted into the mammalian expression vector pRK5, the construction of which is described in EP Pub. No. 307,247, published 15 Mar. 1989. This cDNA starts at nucleotide position 64 of the sequence reported by Loetscher et al., with the initiating methionine 118 bp downstream.

The source of the IgG$_1$ encoding sequence was the CD4-IgG expression plasmid pRKCD4$_2$F$_{c1}$ [Capon, D. J. et al., Nature 337, 525 (1989); Byrn et al., Nature 344, 667 (1990)], containing a cDNA sequence encoding a hybrid polypeptide consisting of residues 1–180 of the mature human CD4 protein (two N-terminal CD4 variable domains) fused to human IgG$_1$ sequences beginning at aspartic acid 216 (taking amino acid 114 as the first residue of the heavy chain constant region [Kabat et al., Sequences of Proteins of Immunological Interest 4th edition (1987)]which is the first residue of the IgG$_1$ hinge after the cysteine residue involved in heavy-light chain bonding), and ending with residue 441 to include the C$_H$2 and C$_H$3 Fc domains of IgG$_1$.

TNFR1-IgG$_1$ was constructed by generating restriction fragments of plasmids pRK-TNF-R and pRKCD4$_2$F$_{c1}$ and ligating them, using deletional mutagenesis, so that threonine residue 171 of mature TNFR's is juxtaposed to aspartic acid residue 216 of IgG$_1$ heavy chain [Kabat et al., Supra]. The resulting plasmid pRKTNFR-IgG contained the full length coding sequence for TNFR$_1$ IgG$_1$.

C. Cell Culture

The gene encoding the soluble type 1 TNFR-IgG$_1$ was introduced into dp12.CHO cells by transfection. This was accomplished using the calcium phosphate technique for introducing DNA into mammalian cells. Two days following transfection the cells were trypsinized and replated into selective medium (glycine-hypoxanthine and thymidine free Ham's F-12 DMEM, 1:1 v/v with 2% dialyzed serum). Subsequent isolates were screened for secretion of TNFR1-IgG$_1$. Clones expressing TNFR1-IgG$_1$ where amplified in methotrexate yielding high expressing clones and subsequently adapted to serum free medium. These cells were under a continuous selective pressure until transferred to nonselective medium for growth and expansion of the inoculum.

To provide cells for TNFR1-IgG$_1$ production cultures the cell population described above was expanded from the medium containing methotrexate by serial subcultivations in vessels of increasing volumes to growth medium containing no methotrexate. For these steps of the process the non selective growth medium was DMEM/HAM F-12 based formulation (see U.S. Pat. No. 5,122,469, for example) with modified concentrations of some components, such as glucose, amino acids, salts, sugar, vitamins glycine, hypoxanthine, and thymidine; recombinant human insulin, hydrolyzed peptone (Primatone HS or Primatone RL), a cell protective agent such as Pluronic F68 (pluronic polyol) or the equivalent; gentamycin; Lipid and trace elements.

The cultures were controlled at pH 7.2±0.4 by the use of CO$_2$ gas (acid) and /or Na$_2$CO$_3$ (base). Temperature was controlled near 37° C. during the growth period. Dissolved oxygen was maintained above 5% of air saturation by direct sparging with air and/or oxygen gas.

The osmolality during the inoculum expansion phase was maintained between about 250 mOsm and 350 mOsm.

The growth phase for each culture was followed by a second phase or transition phase wherein culture parameters were changed from optimal growth to production conditions. During this transition phase the temperature of the culture system was decreased, generally to about between 30° and 35 ° C. Butyrate was added and a certain osmolality range was engaged. Product accumulated during this production phase was analyzed for sialic acid content.

In a typical production schedule approximately 1.2×10$^6$ cells derived from the inoculum expansion from the selective stage where grown in a growth phase with a starting osmolality of 300 mOsm. The growth medium was supplemented with trace elements, recombinant human insulin and hydrolyzed peptone. The cells were grown under these condition for 2 days. At the start of the third day the temperature of the cell culture was lowered. Simultaneous to or following the temperature shift, sodium butyrate was added to the cell culture and the desired production osmolality was engaged by addition of various media components. Cells were grown under these conditions with feeding for 9–10 days. The cells were fed when necessary with various media components.

Table I describes the production conditions for various production processes.

TABLE I

| Process version | Butyrate concentration (mmol/l) | Osmolality in production phase (mOsmol/kg) | Cell specific productivity between day 5 and day 10 (pg/d) | Sialic acid content of TNFR1-IgG$_1$ on day 10 (mol/mol) | |
|---|---|---|---|---|---|
| A | 1 | 360–420 | 0.6–1.5 | 6.4–7.2 | N = 4 |
| B | 1 | 480–510 | 1.7–2.2 | 6.0–6.3 | N = 3 |
| C | 6 | 460 | 4.8 | 4.7 | N = 1 |
| D | 6 | 370–420 | 2.4–2.8 | 5.5–5.6 | N = 3 |
| E | 6 | 350–370 | 1.4–2.3 | 5.4–6.3 | N = 3 |
| F | 12 | 390 | 4.0 | 5.3 | N = 1 |
| G | 12 | 490–510 | 2.9–5.2 | 4.0–5.2 | N = 4 |
| H | 12 | 400–430 | 2.0–2.8 | 5.8–6.0 | N = 3 |
| I | 12 | 370–380 | 2.0–2.2 | 5.5–5.9 | N = 3 |

D. Recovery of the TNFR-IgG

The TNFR1-IgG$_1$ chimera was purified to greater than 95% homogeneity by affinity chromatography on immobilized Staphylococcus aureus Protein A as described by Capon et al., Supra.

E. Carbohydrate Analysis

Sialic acid content was analyzed by the method of Warren, L. (1959) J. Biol. Chem. 234:1971–1975.

Results

Cell specific productivity for each of the production cultures described in Table I was plotted against the sialic acid content of the harvested product. The results are presented in FIG. 1. The highest sialic acid content was observed when process parameters where maintained at a production osmolality of between about 360 and 420 mOsm. and a butyrate concentration of about 1 mM. Sialic acid content could be controlled over a wide range of values by adjusting the process parameters.

EXAMPLE II

Plasma pharmacokinetic half-lives and/or clearance rates of different preparations were determined. The preparations containing a higher sialic acid content in general exhibited increased plasma half-life and/or lower total clearance rates compared to preparations containing a decreased sialic acid content.

Methods

Seventeen male Sprague-Dawley-derived rats weighing 272–315 g were randomly assigned to one of three TNFR1-IgG$_1$ fusion protein treatment groups (N=5 or 6 per group). The animals were injected intravenously with a nominal dose of 5 mg/kg of test material via a femoral vein cannula. The test materials chosen included two TNFR1-IgG$_1$ preparations from a process in which the butyrate concentration during the production phase was 6 mM and the osmolality during the production phase was maintained at about 400 mOsm, Process I, and a third TNFR1-IgG$_1$ preparation from a process in which the butyrate concentration was 12 mM and the osmolality during the production phase was about 500 mOsm, Process II. Two mL blood samples were collected onto EDTA (8.5%) pre-dose, and at 5 min, and 2, 6, 10, 24, 34, 48, 56, 72, 96, and 120 hours post-dose. Blood samples were centrifuged, plasma harvested, and the samples analyzed for concentrations of TNFR1-IgG$_1$ fusion protein.

An enzyme-linked immunological and biological binding assay (ELIBA) was used to quantitate TNFR1-IgG$_1$ in rat plasma. This assay is based on the ability of TNF-alpha coupled to horseradish peroxidase (TNF-alpha-HRP) to bind to the receptor portion of the TNFR1-IgG$_1$ fusion protein. In this assay, Fab fragments of goat antihuman IgGFc coated on wells of microtiter plates were used to capture TNFR1-IgG$_1$ by interaction with the Fc portion of the molecule. TNF-alpha-HRP was added to the wells and allowed to bind to the receptor portion of the captured TNFR1-IgG$_1$. Quantification was determined by measurement of a color produced by reaction of peroxidase with peroxide and an ortho-phenylenediamine (OPD) substrate. The range of the assay is 0.003 to 0.02 mg/mL. The presence of EDTA in the plasma samples was shown to have no effect on the performance of the assay.

The dose was normalized to account for dosing solution concentration differences. All calculations were based on concentration versus time data through the 120-hr timepoint. Truncated area under the curve (AUC$_{0-120}$) was calculated using the trapezoidal rule and weight-normalized truncated clearance (CL$_{0-120}$/W) was calculated as dose/AUC$_{0-120}$.

Results

Clearance rates varied depending upon the process version utilized (Process I compared to Process II) and the amount of sialic acid present in the product. Clearance rates for individual animals and the resulting mean and standard deviations from this study are presented in Table II below. Process I exhibits a slower and more favorable clearance rate.

TABLE II

| | CLEARANCE 0–120 (mL/hr/kg) | | |
|---|---|---|---|
| | Process I | Process I | Process II |
| | 2.12 | 2.08 | 2.144 |
| | 2.03 | 2.31 | 2.99 |
| | 1.63 | 2.20 | 2.61 |
| | 1.89 | 2.22 | 3.27 |
| | 1.85 | 1.99 | 2.82 |
| | | 1.66 | 3.42 |
| mean | 1.91 | 2.08 | 2.88 |
| STDEV | 0.02 | 0.23 | 0.45 |

EXAMPLE III

MONOSACCHARIDE COMPOSITION OF TNFR1-IgG$_1$

Determination of oligosaccharide carbohydrate composition and structure of TNFR1-IgG$_1$, prepared as described in Example 1 showed that the sialic acid content of the various process version varied. Rapid plasma clearance was associated with high exposed GlcNAc, lower sialic acid on the oligosaccharide chains and (by inference) accessibility of the protein to mannose or galactose receptors. Slow plasma clearance was associated with more terminal sialic acid residues.

A. Sources of Test Material

TNFR1-IgG$_1$ was produced according to the methods outlined as described in Example 1 above. Process I material was obtained from cell culture using 6 mM butyrate and an osmolality of about 400 mOsm during the production phase. Process material II was obtained from cell culture using 12 mM butyrate and an osmolality of about 500 mOsm during the production phase.

B. Methods

Release of intact neutral and amino-sugars was determined by high pH anion-exchange chromatography combined with pulsed amperometric detection. Analysis was performed using the following steps:

1. Buffer exchange was performed with TNFR1-IgG$_1$ (approximately 50 µg/ml) and the appropriate reference samples so that the final sample was contained in 1% acetic acid.
2. Approximately 90 µg TNFR1-IgG$_1$ as well as samples of reference materials were frozen in a dry ice and alcohol bath and the frozen sample lyophilized overnight.
3. The freeze dried samples were reconstituted in 500 µl trifluoroacetic acid and incubated at 120° C. for 1 hour.
4. After acid hydrolysis the TNFR1-IgG$_1$ and reference samples were cooled and evaporated to dryness.
5. Samples were reconstituted with water to a final concentration of approximately 0.6 mg/ml.
6. Separation of the monosaccharides was performed at ambient temperature by high pH anion exchange chromatography with pulsed amperometric detection using a Dionex CarboPac PA1 (4×250 mm) column (Dionex Corp., Sunnyvale, Calif.).
7. Quantitation of individual monosaccharides was by comparison to reference monosaccharides.

C. Results

The relative molar content of each monosaccharide in the two preparations are shown in Table III, below.

TABLE III

RELATIVE MOLAR CONTENT OF MONOSACCHARIDES IN TWO TNFR1-IgG₁ PREPARATIONS

| Monosaccharide | Process I | Process II |
|---|---|---|
| Fucose | 4.3 ± 0.2 | 4.4 |
| Galactose | 6.5 ± 0.0 | 4.7 |
| Mannose | 12.2 ± 0.6 | 12.5 |
| N-acetylglucosamine | 14.1 ± 0.6 | 14.3 |
| Sialic acid | 4.9 ± 0.3 | 3.7 ± 0.3 |
| N-acetylgalactosamine | 0.5 ± 0.1 | 0.3 |
| Ratio sialic acid/GlcNAc | 0.35 | 0.26 |

The above results demonstrate that the process parameters selected for the production phase of the glycoprotein affect the carbohydrate composition of the mature glycoprotein. Preparations having a higher sialic acid content generally exhibited prolonged serum half-life.

Tables IV and V presented below demonstrate the carbohydrate composition of the oligosaccharide side chains of the TNFR1-IgG₁ chimera preparations produced under process I and process II type conditions. Table V presents data for carbohydrates on the receptor portion of the chimeric molecule, subtracting the $F_c$ glycosylation site.

TABLE IV

|  | PI | PI | PI | PI | PII | PII |
|---|---|---|---|---|---|---|
| Sialic Acid | 5.8 | 5.8 | 5.7 | 5.8 | 3.7 | 3.5 |
| Fucose | 4.0 | 4.0 | 3.6 | 4.1 | 4.4 | 4.3 |
| Gal NAc | 0.3 | 0.2 | 0.2 | 0.4 | 0.3 | 0.4 |
| Glc NAc | 12.9 | 15.0 | 14.8 | 14.3 | 14.3 | 14.4 |
| Gal | 7.4 | 7.6 | 7.1 | 7.0 | 4.7 | 4.1 |
| Man | 12.0 | 12.0 | 10.0 | 12.0 | 12.5 | 11.9 |
| Ratio SA/GlcNAc | 0.45 | 0.39 | 0.39 | 0.41 | 0.26 | 0.24 |

TABLE V

|  | PII | PII | PI | PI |
|---|---|---|---|---|
| Moles exposed GlcNAc per mole | 3.18 | 3.2 | 1.11 | 1.32 |
| Moles exposed Gal per mole | 0.97 | −0.08 | 1.45 | −0.26 |
| Gal antennae | 4.47 | 4.72 | 6.45 | 6.24 |
| Sialic acid per mole | 3.5 | 4.8 | 5.00 | 6.5 |

The results presented in Table IV and V demonstrate that the composition of the TNFR1-IgG₁ are typical of sialic acid terminated mono- bi- and triantennary complex oligosaccharides. It can be concluded that the TNFR1-IgG₁ prepared by Process I contains a significantly higher proportion of sialic acid and a significantly lower proportion of exposed GlcNAc. Sialic acid per mole protein indicates that this material would have a lower isoelectric point than the material produced by Process II. By comparison with the results in Table II, these results also indicate that the slower plasma clearance of Process I material correlates with lower exposed GlcNAc and generally with a higher sialic acid content.

Table IV and V demonstrate TNFR1-IgG₁ preparations comprising a complex oligosaccharide terminated by one or more residues of a sialic acid. The preferred TNFR1-IgG₁ preparations comprise TNFR1-IgG1 molecules having about 1–2 moles of exposed N-acetylglucosamine residues per mole of protein. The molar ratio of sialic acid to protein is about 4–7. The TNFR1-IgG₁ preparations have a molar ratio of sialic acid to N-acetylglucosamine of about 0.4 to about 0.45.

EXAMPLE IV

The pI of the heavily sialylated preparation is lower than the pI of the lightly sialylated preparation.

Methods

Isoelectric focusing was performed for the various preparation described in Example II. The isoelectric focusing gels separate the glycoproteins of the preparation according to their isoelectric point, pI, using a pH gradient created with ampholytes of different pH. In this study, analysis of the preparations was performed using a pH gradient of 10 to 4.

Results

The TNFR1-IgG₁ preparations exhibit an isoelectric point range, of about 5.5 to about 7.5 as determined by chromatofocusing, in which the pI is sensitive to neuraminidase treatment.

The references cited above are all incorporated by reference herein, whether specifically incorporated or not.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A process for controlling the amount of sialic acid present on an oligosaccharide side chain of a glycoprotein produced by culture in a mammalian host cell which comprises:
   culturing the mammalian host cell in a production phase of the culture which is characterized by:
   i) adding an alkanoic acid or a salt thereof to the culture at a concentration of about 0.1 mM to about 20 mM;
   ii) maintaining the osmolality of the culture at about 250 to about 600 mOsm; and
   iii) maintaining the temperature of the culture at a temperature about between 30° C. and 35° C.

2. The process of claim 1 wherein the production phase is a batch or fed batch culture phase.

3. The process of claim 2 where the production phase is preceded by a transition phase during which the temperature is lowered to about between 30° C. and 35° C. before the production phase begins.

4. The process according to claim 1 wherein the amount of sialic acid present on the oligosaccharide side chain of the glycoprotein is increased and wherein; cell specific productivity of the cell culture is decreased by culturing the host cell at a concentration of the alkanoic acid or salt thereof of about 1 to about 6 mM and maintaining the osmolality at about 300–450 mOsm.

5. The process of claim 4 wherein the production phase is a batch or fed batch culture phase.

6. The process of claim 5 where the production phase is preceded by a transition phase during which the temperature is lowered to about between 30° C. and 35° C. before the production phase begins.

7. The process of claim 6 in which the host cell is a CHO cell.

8. The process of claim 7 in which the host cell is a dhfr⁻CHO cell.

9. The process according to claim 8 wherein the alkanoic acid or salt thereof is sodium butyrate.

10. The process according to claim 9 wherein the glycoprotein produced is a mammalian glycoprotein.

11. The process according to claim 10 wherein the glycoprotein is a tumor necrosis factor receptor-immunoglobulin chimera.

12. The process of claim 11 in which the host cell is a cell transfected with a vector carrying the cDNA for a soluble type 1 tumor necrosis factor receptor-immunoglobin $G_1$ TNFR1-IgG$_1$ chimera.

13. The process according to claim 1 wherein the amount of sialic acid present on the oligosaccharide side chain of the glycoprotein is decreased and wherein;

cell specific productivity of the cell culture is increased by culturing the host cell at a concentration of about 6 mM to about 12 mM of the alkanoic acid or salt thereof and maintaining the osmolality at about 450–600 mOsm.

14. The process of claim 13 wherein the production phase is a batch or fed batch culture phase.

15. The process of claim 14 where the production phase is preceded by a transition phase during which the temperature is lowered to about between 30° C. and 35° C. before the production phase begins.

16. The process of claim 15 in which the host cell is a CHO cell.

17. The process of claim 16 in which the host cell is a dhfr⁻CHO cell.

18. The process according to claim 17 wherein the alkanoic acid or salt thereof is sodium butyrate.

19. The process according to claim 18 wherein the glycoprotein produced is a mammalian glycoprotein.

20. The process according to claim 19 wherein the glycoprotein is a tumor necrosis factor receptor-immunoglobulin chimera.

21. The process of claim 20 in which the host cell is a cell transfected with a vector carrying the cDNA for a soluble type 1 tumor necrosis factor receptor-immunoglobin $G_1$ TNFR1-IgG$_1$ chimera.

* * * * *